United States Patent
Dodd et al.

(10) Patent No.: US 11,253,350 B2
(45) Date of Patent: *Feb. 22, 2022

(54) LIGAMENT ASSEMBLY

(71) Applicants: Biomet UK Healthcare Limited, Bridgend (GB); Christopher Dodd, Oxford (GB); David Wycliffe Murray, Oxford (GB); John O'Connor, Oxford (GB)

(72) Inventors: Christopher Dodd, Oxford (GB); David Wycliffe Murray, Oxford (GB); John O'Connor, Oxford (GB); Russell Lloyd, Swindon (GB); Mona Alinejad, London (GB)

(73) Assignee: Biomet UK Healthcare Limited, Bridgend (GB)

( * ) Notice: Subject to any disclaimer, the term of this patent is extended or adjusted under 35 U.S.C. 154(b) by 108 days.

This patent is subject to a terminal disclaimer.

(21) Appl. No.: 16/676,008

(22) Filed: Nov. 6, 2019

(65) Prior Publication Data

US 2020/0069413 A1    Mar. 5, 2020

Related U.S. Application Data

(63) Continuation of application No. 15/962,718, filed on Apr. 25, 2018, now Pat. No. 10,500,037, which is a
(Continued)

(30) Foreign Application Priority Data

Aug. 12, 2013 (GB) .................................. 1314410

(51) Int. Cl.
*A61F 2/08* (2006.01)
*A61F 2/38* (2006.01)
*A61F 2/30* (2006.01)

(52) U.S. Cl.
CPC .............. *A61F 2/0811* (2013.01); *A61F 2/38* (2013.01); *A61F 2/3836* (2013.01);
(Continued)

(58) Field of Classification Search
CPC ........ A61F 2/08; A61F 2/0811; A61F 2/3859; A61F 2/38
See application file for complete search history.

(56) References Cited

U.S. PATENT DOCUMENTS 5,556,428 A  9/1996 Shah
5,769,893 A  6/1998 Shah
(Continued)

FOREIGN PATENT DOCUMENTS

CN    1218381 A    6/1999
CN    101879099 A   11/2010
(Continued)

OTHER PUBLICATIONS

"U.S. Appl. No. 14/911,493, Non Final Office Action dated Jul. 10, 2017", 6 pgs.
(Continued)

*Primary Examiner* — Jason-Dennis N Stewart
(74) *Attorney, Agent, or Firm* — Schwegman Lundberg & Woessner, P.A.

(57) ABSTRACT

A ligament assembly (2) comprising a resilient element (20) connected to a bone anchor (4) and a ligament (18), the resilient element (20) acting m a cantilever and resisting toads transmitted between the bone anchor (4) and the ligament (18) by virtue of the resistance to bending of the resilient element. The ligament (18) may comprise an artificial ligament (18) which is adapted to replace a human or animal ligament. The resilient element (20) may comprise a spiral spring and may act as a biasing element/shock absorber operatively coupled to the artificial ligament (18) to
(Continued)

control the effective stiffness of the artificial ligament (18). Consequently, the resilient element (20) enables an effective stiffness of the artificial ligament (18) to be achieved that more closely approximates the stiffness of a natural ligament.

19 Claims, 3 Drawing Sheets

Related U.S. Application Data continuation of application No. 14/911,493, filed as application No. PCT/GB2014/052350 on Jul. 31, 2014, now Pat. No. 9,980,808.

(52) U.S. Cl.
CPC ............... *A61F 2002/0852* (2013.01); *A61F 2002/30462* (2013.01); *A61F 2002/30481* (2013.01); *A61F 2002/30573* (2013.01); *A61F 2220/0008* (2013.01)

(56) References Cited

U.S. PATENT DOCUMENTS

| | | |
|---|---|---|
| 9,980,808 B2 | 5/2018 | Dodd et al. |
| 10,149,767 B2 | 12/2018 | Metzger et al. |
| 10,500,037 B2 | 12/2019 | Dodd et al. |
| 2004/0054409 A1 | 3/2004 | Harris |
| 2007/0100462 A1 | 5/2007 | Lang et al. |
| 2009/0275981 A1 | 11/2009 | Abdelgany et al. |
| 2010/0305709 A1 | 12/2010 | Metzger et al. |
| 2012/0078369 A1 | 3/2012 | Hart |
| 2012/0283831 A1 | 11/2012 | Murray |
| 2012/0296427 A1 | 11/2012 | Conner et al. |
| 2013/0053958 A1 | 2/2013 | Macossay-torres |
| 2014/0081276 A1 | 3/2014 | Lizardi et al. |
| 2014/0156004 A1 | 6/2014 | Shenoy et al. |
| 2014/0156005 A1 | 6/2014 | Shenoy et al. |
| 2015/0127048 A1 | 5/2015 | Curtis et al. |
| 2015/0366672 A1 | 12/2015 | Delsignore |
| 2015/0374390 A1 | 12/2015 | Amis et al. |
| 2016/0199171 A1 | 7/2016 | Dodd et al. |
| 2016/0250014 A1 | 9/2016 | Williams et al. |
| 2017/0252171 A9 | 9/2017 | Kaufmann |
| 2018/0235748 A1 | 8/2018 | Dodd et al. |

FOREIGN PATENT DOCUMENTS

| | | |
|---|---|---|
| CN | 102670293 A | 9/2012 |
| CN | 105555226 A | 5/2016 |
| GB | 2454251 A | 5/2009 |
| GB | 2464862 A | 5/2010 |
| GB | 2517154 A | 2/2015 |
| JP | 2001015236 A | 1/2001 |
| JP | 2011502608 A | 1/2011 |
| JP | 2013526380 A | 6/2013 |
| JP | 2013527006 A | 6/2013 |
| JP | 2016527066 A | 9/2016 |
| JP | 2019141662 A | 8/2019 |
| KR | 20060117762 A | 11/2006 |
| SU | 1351598 A1 | 11/1987 |
| WO | WO-2004017845 A1 | 3/2004 |
| WO | WO-2011041783 A1 | 4/2011 |
| WO | WO-2012019248 A1 | 2/2012 |
| WO | WO-2012027656 A1 | 3/2012 |
| WO | WO-2015022492 A1 | 2/2015 |

OTHER PUBLICATIONS

"U.S. Appl. No. 14/911,493, Notice of Allowance dated Jan. 29, 2018", 5 pgs.
"U.S. Appl. No. 14/911,493, Notice of Allowance dated Feb. 12, 2018", 2 pgs.
"U.S. Appl. No. 14/911,493, Preliminary Amendment filed Feb. 11, 2016", 7 pgs.
"U.S. Appl. No. 14/911,493, Response filed Oct. 10, 2017 to Non Final Office Action dated Jul. 10, 2017", 9 pgs.
"U.S. Appl. No. 15/962,718, Advisory Action dated Apr. 11, 2019", 3 pgs.
"U.S. Appl. No. 15/962,718, Final Office Action dated Feb. 27, 2019", 8 pgs.
"U.S. Appl. No. 15/962,718, Non Final Office Action dated Oct. 18, 2018", 6 pgs.
"U.S. Appl. No. 15/962,718, Notice of Allowability dated Oct. 21, 2019", 4 pgs.
"U.S. Appl. No. 15/962,718, Notice of Allowance dated Aug. 6, 2019", 5 pgs.
"U.S. Appl. No. 15/962,718, Response filed Nov. 29, 2018 to Non Final Office Action dated Oct. 18, 2018", 10 pgs.
"U.S. Appl. No. 15/962,718, Response filed Apr. 1, 2019 to Final Office Action dated Feb. 27, 2019", 7 pgs.
"Australian Application Serial No. 2014307790, First Examination Report dated May 7, 2018", 4 pgs.
"Australian Application Serial No. 2014307790, Response filed Jul. 3, 2018 to First Examination Report dated May 7, 2018", 34 pgs.
"Canadian Application Serial No. 2,920,867, Examiner's Rule 30(2) Requisition dated Oct. 3, 2019", 4 pgs.
"Chinese Application Serial No. 201480051473.2, Office Action dated Aug. 10, 2017", (W/English Translation), 6 pgs.
"Chinese Application Serial No. 201480051473.2, Office Action dated Nov. 28, 2016", (W/English Translation), 16 pgs.
"Chinese Application Serial No. 201480051473.2, Response filed May 2, 2017 to Office Action dated Nov. 28, 2016", (W/ English Translation), 10 pgs.
"Chinese Application Serial No. 201480051473.2, Response filed Oct. 10, 2017 to Office Action dated Aug. 10, 2017", (W/English Translation of Claims), 23 pgs.
"European Application Serial No. 14750605.9, Communication Pursuant to Article 94(3) EPC dated Oct. 26, 2017", 6 pgs.
"European Application Serial No. 14750605.9, Response filed Mar. 5, 2018 to Communication Pursuant to Article 94(3) EPC dated Oct. 26, 2017", 11 pgs.
"European Application Serial No. 14750605.9, Response filed Oct. 10, 2016 to Communication pursuant to Rules 161(1) and 162 EPC dated Mar. 29, 2016", 10 pgs.
"International Application Serial No. PCT/GB2014/052350, International Preliminary Report on Patentability dated Nov. 16, 2015", 8 pgs.
"International Application Serial No. PCT/GB2014/052350, International Search Report dated Oct. 24, 2014", 5 pgs.
"International Application Serial No. PCT/GB2014/052350, Written Opinion dated Oct. 24, 2014", 7 pgs.
"Japanese Application Serial No. 2016-533947, Final Notification of Reasons for Refusal dated Jan. 29, 2019", (W/ English Translation), 5 pgs.
"Japanese Application Serial No. 2016-533947, Office Action dated Jun. 26, 2018", w/ English translation, 9 pgs.
"Japanese Application Serial No. 2016-533947, Response filed Oct. 4, 2018 to Office Action dated Jun. 26, 2018", (W/ English Claims), 17 pgs.
"United Kingdom Application Serial No. 1314410.0, Office Action dated Aug. 13, 2019", 6 pgs.
"Canadian Application Serial No. 2,920,867, Response filed Mar. 31, 2020 to Examiner's Rule 30(2) Requisition dated Oct. 3, 2019", 12 pgs.
"European Application Serial No. 19208700.5, Extended European Search Report dated Feb. 2, 2021", 10 pgs.
"Japanese Application Serial No. 2019-079403, Notification of Reasons for Rejection dated Jan. 5, 2021", w/ English Translation, 7 pgs.
"Japanese Application Serial No. 2019-079403, Notification of Reasons for Rejection dated Mar. 17, 2020", w/ English translation, 10 pgs.

(56) References Cited

OTHER PUBLICATIONS

"Japanese Application Serial No. 2019-079403, Response filed Apr. 1, 2021 to Notification of Reasons for Rejection dated Jan. 5, 2021", w/ English claims, 7 pgs.

"Japanese Application Serial No. 2019-079403, Response filed Jul. 15, 2020 to Notification of Reasons for Rejection dated Mar. 17, 2020", w/ English claims, 9 pgs.

"European Application Serial No. 19208700.5, Response filed Sep. 1, 2021 to Extended European Search Report dated Feb. 2, 2021", 16 pages.

LIGAMENT ASSEMBLY

This invention relates to a ligament assembly comprising a resilient element connected to a bone anchor and a ligament, the resilient element acting as a cantilever and resisting loads transmitted between the bone anchor and the ligament by virtue of the resistance to bending of the resilient element.

BACKGROUND

It is known to reattach a damaged ligament using a conventional bone anchor. It is also known to implant an artificial ligament to replace a natural ligament which has become damaged. Conventional artificial ligaments are formed from strands or bundles of artificial fibres which may be woven and/or aligned to form a flexible member which is substantially uniform in size and is resilient along its length.

A natural ligament exhibits high strength, toughness and resilience and retains these properties for many years. To date, it has been impossible to match these properties using artificial fibres.

When implanted, artificial ligaments may be attached to existing bone tissue, provided the tissue at the attachment site is relatively intact. However, if surrounding bone tissue is diseased or damaged, it may be necessary to remove both the natural ligament and the adjacent bone tissue and replace them with prosthetic components.

Joint replacement operations commonly result in removal of at least one ligament. The functionality of the ligament is replicated as closely as possible by one or more features of the replacement prosthesis (as for example in the case of a cooperating cam and post in a total knee replacement). However, it has proved extremely difficult to replicate the natural kinematics of a joint without the presence of naturally functioning ligaments. This is particularly evident in the case of the knee joint, which exhibits a complex movement that is highly dependent upon the interaction of ligaments with the articulating areas of bone.

SUMMARY OF INVENTION

According to an aspect of the present invention, there is provided a ligament assembly comprising a resilient element connected to a bone anchor and a ligament, the resilient element resisting loads transmitted between the bone anchor and the ligament by virtue of the resistance to bending of the resilient element.

The ligament assembly may further comprise the said bone anchor.

The resilient element may be fixed to the bone anchor at or towards a first end only, and/or may be loaded at or towards an opposite end only.

The resilient element may comprise a spring, such as a cantilever spring, a spiral spring, a leaf spring or an elongate elastic member acting as a form of spring. In its simplest form, the resilient element may comprise an elastic member, such as an elongate sprung steel beam and may be cast, machined or otherwise formed in one piece.

The resilient element may be attached at or towards a first end to the bone anchor. The first end may be a radially inner end, if the resilient element is a spiral spring.

The bone anchor may comprise a component of a joint replacement prosthesis.

The bone anchor may be provided with a bore in which the resilient element is at least partially received. Opposite sides of the bore may be provided with recesses which are adapted to receive projections formed on the resilient element. A clip may be provided which engages in the bone anchor, provides a stop for at least one of the projections and/or retains the resilient element in the bore. The dip may be substantially U-shaped and may have a pair of spaced apart legs connected together by a web. The legs may engage on opposite sides of the resilient element to ensure balanced retention of the projections. The dip may engage in one or more grooves formed in the bone anchor. The grooves may be adjacent a mouth of the bore.

The resilient element may have a ligament engaging portion at or towards a free end of the resilient element. The ligament engaging portion comprises a bollard attached to or integrally formed with the resilient element.

The ligament assembly may further comprise a ligament adapted for attachment to the resilient element. The ligament may comprise a loop which fits over a bollard formed on the resilient element.

The resilient element may be formed from biocompatible material such as stainless steel or titanium.

The resilient element may have a stiffness approximating that of a natural ligament that is to be replaced.

According to another aspect of the present invention, there is provided a method of implanting a ligament assembly comprising a resilient element, the method comprising:
  a) implanting a bone anchor into a bone;
  d) fixing a resilient element in a bore formed in the bone anchor;
  e) connecting an end of a ligament to the resilient element such that the resilient element acts as a cantilever and resists loads transmitted between the bone anchor and the ligament by virtue of the resistance to bending of the resilient element.

According to another aspect of the present invention, there is provided a kit of parts comprising a ligament assembly as claimed in any preceding claim and a plurality of interchangeable resilient elements, each resilient element in the set having a different resistance to bending from the other resilient elements in the set.

According to another aspect of the present invention, there is provided a ligament assembly comprising a spiral spring. The ligament assembly may further comprise a bone anchor and/or an artificial ligament which is adapted to replace a human or animal ligament. The spiral spring may act as a biasing, tensioning and/or shock absorbing element operatively coupled to the artificial ligament to control the effective stiffness of the artificial ligament. Consequently, the spiral spring enables an effective stiffness of the artificial ligament to be achieved that more closely approximates the stiffness of a natural ligament.

The spiral spring may be operatively coupled to the ligament at or near one end only of the ligament.

The spiral spring may engage the ligament via a bearing component such as a bollard formed on an outer end of the spiral spring.

The spiral spring may have a stiffness approximating that of a natural ligament that is to be replaced. In this manner, the spiral spring may assist in replicating the natural characteristics of the joint. The spiral spring may have linear or non-linear stiffness characteristics. For example, the spiral spring may have a buffer element attached to a first coil and located between the first coil and a second coil of the spiral spring, such that there is some clearance between the buffer element and the second coil when the spiral spring is unloaded. When the spiral spring is under a predetermined load, the buffer element may abut the second coil to thereby stiffen the spiral spring, resulting in a non-linear stiffness characteristic without exceeding the elastic limit of the spiral spring.

The ligament may be coupled to the spiral spring via an attachment means. The attachment means may comprise an enlarged portion that is formed on the ligament and engages the spiral spring. For example, the enlarged portion may comprise a loop or knot formed in the artificial ligament.

The prosthesis may further comprise a bone engaging element for attachment to a bone. The spiral spring may act between the bone engaging element and the artificial ligament.

The spiral spring may be at least partially housed within the bone engaging element. The bone engaging element may comprise a stem, and the spiral spring may be at least partially housed within the stem.

The spiral spring may comprise one of a set of interchangeable spiral springs, each spring in the set being of different dimensions and/or stiffness. An appropriate one of the spiral springs may be selected to achieve a desired ligament tension and/or balance in a particular patient.

The ligament assembly may comprise at least part of a joint replacement prosthesis, which may be a knee replacement prosthesis.

The ligament assembly may comprise at least part of a knee replacement prosthesis in which the bone anchor comprises a tibial component and the ligament comprises a replacement anterior cruciate ligament (ACL).

According to another aspect of the present invention, there is provided a method of implanting a ligament assembly comprising a spiral spring, the method comprising:
  a) implanting a tibial prosthesis into a tibia;
  b) fixing the spiral spring to the tibial prosthesis;
  c) connecting an end of a ligament to the spiral spring.

The step (b) may comprise fixing the spiral spring in a bore formed in the tibial prosthesis.

According to another aspect of the present invention, there is provided a kit of parts comprising a ligament assembly which may be as described above, and a plurality of interchangeable spiral springs, each spiral spring in the set being of a different dimension and/or stiffness from the other spiral springs in the set.

Use of a spiral spring as a means of biasing or tensioning a ligament provides the following technical advantages:
  1) The number of moving elements is minimized, because the spiral spring is self supporting and can be formed with attachment elements for attaching directly to the ligament and the bone anchor.
  2) When used in a knee prosthesis, the spiral spring can be positioned along the loading direction of the anterior cruciate ligament (ACL)—approximately 45 degrees at full extension of the knee joint. The angle of an artificial ACL can change in the same way as a natural ACL at different flexion angles as the free end of the spring on the tibial side has the ability to rotate relative to the attachment site on the femur
  3) The stiffness and the amount of deformation of the spiral spring can be changed by changing the number of turns, thickness/width of coil, and distance between the turns.
  4) Right and left spiral springs can be made for right and left knees respectively, to improve the loading direction and connection to the ligament.

BRIEF DESCRIPTION OF THE DRAWINGS

For a better understanding of the present invention, and to show how it may be carried into effect, reference will now be made, by way of example, to the accompanying drawings in which.

DETAILED DESCRIPTION

In this specification, the terms anterior, posterior, lateral and medial are used in relation to a ligament assembly implanted in a patient.

Figure 1:
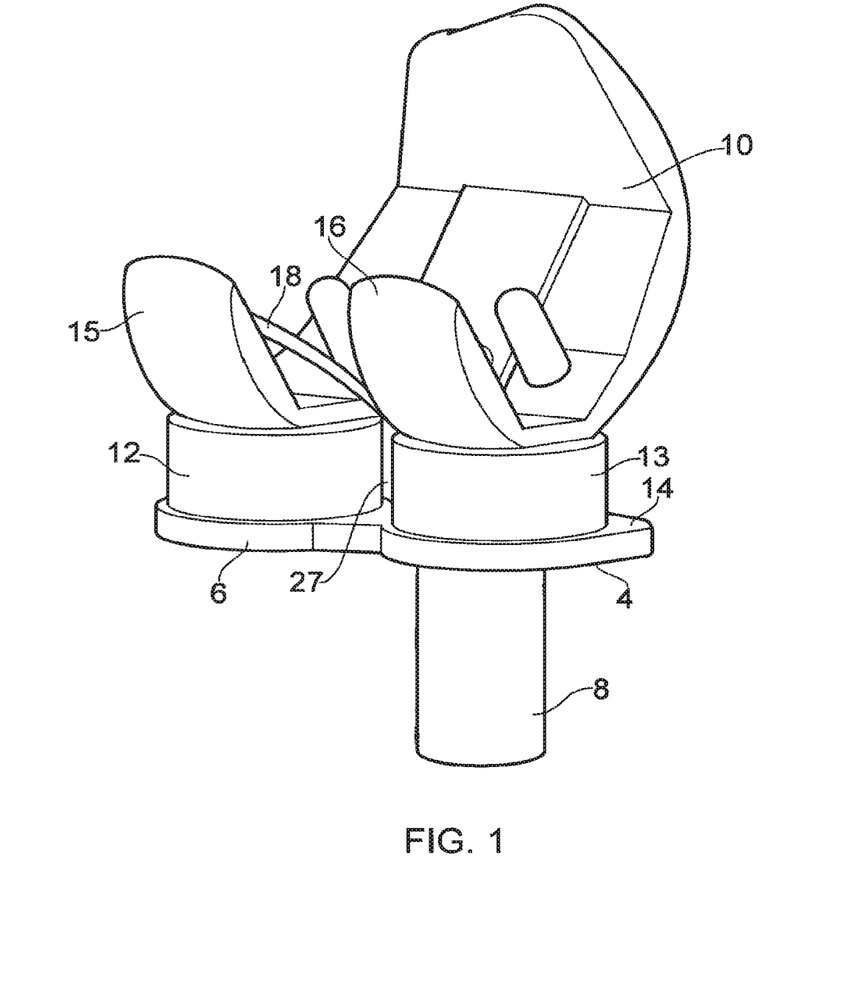
FIG. 1 is a perspective view of a ligament assembly incorporated into a knee prosthesis.
Figure 2:
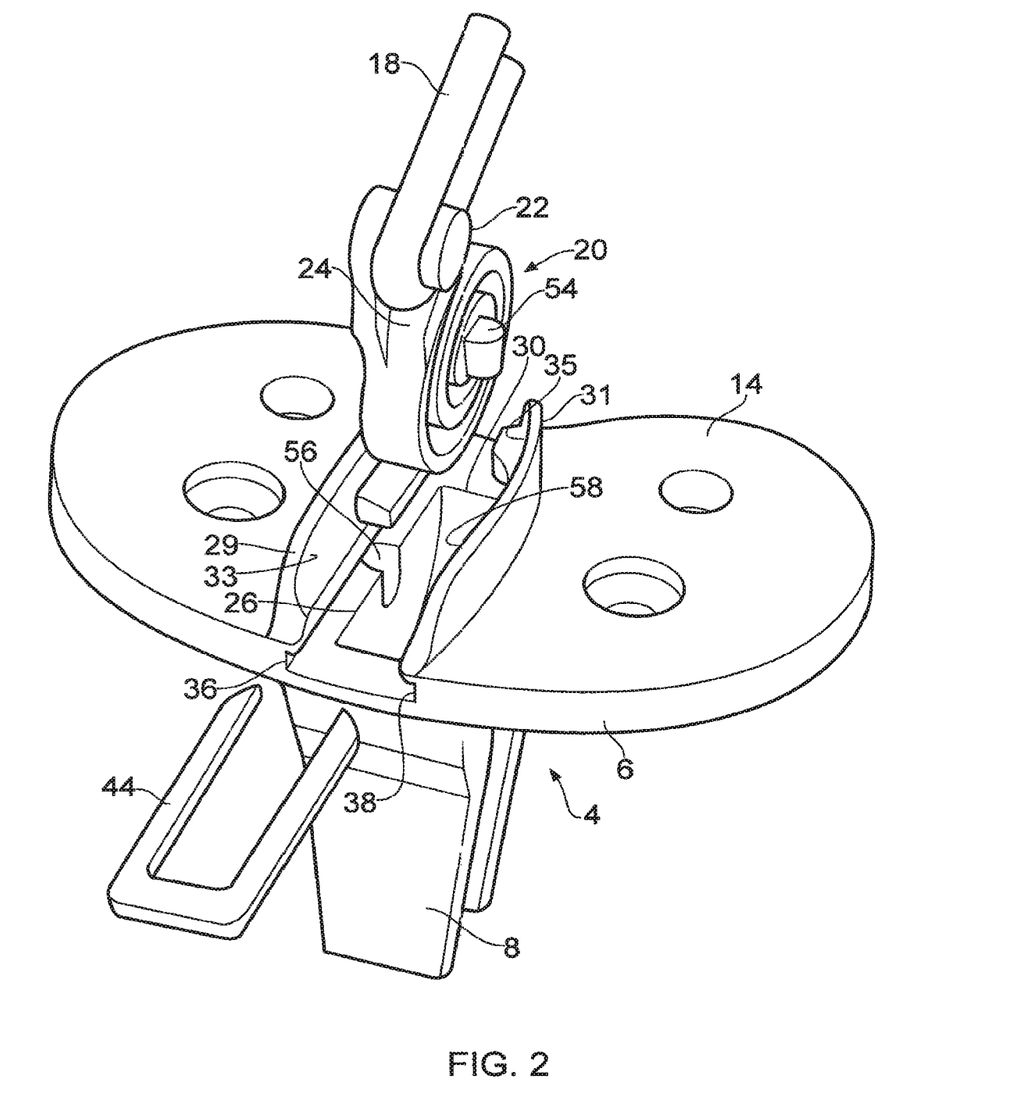
FIG. 2 is a perspective view of a disassembled ligament assembly.

Referring to FIGS. 1 and 2, a knee prosthesis incorporating a ligament assembly 2 comprises a tibial component 4 having a tibial tray 6 integrally formed with a stem 8, a femoral component 10 and a pair of bearing components 12, 13. The bearing components 12, 13 separate the tibial component 4 and femoral component 10, and are formed with proximal and distal bearing surfaces which engage corresponding bearing surfaces 14, 15, 16 on the tibial tray 6 and on the femoral component 10. These various bearing surfaces enable the tibial component 4 to rotate and translate relative to the femoral component 10. One or both of the bearing components 12, 13 may be meniscal bearing components, rotational platform bearing components, or fixed bearing components.

An artificial ligament 18 is connected at one end to the femoral component 10, and at the other end to a tensioning and/or biasing and/or support element comprising a spiral spring 20 mounted in the stem 8 of the tibial component 4. The spiral spring 20 is provided with a bollard 22 at its radially outer end 24 which is adapted to receive an end of the ligament 18.

Figures 3, 4, 5:
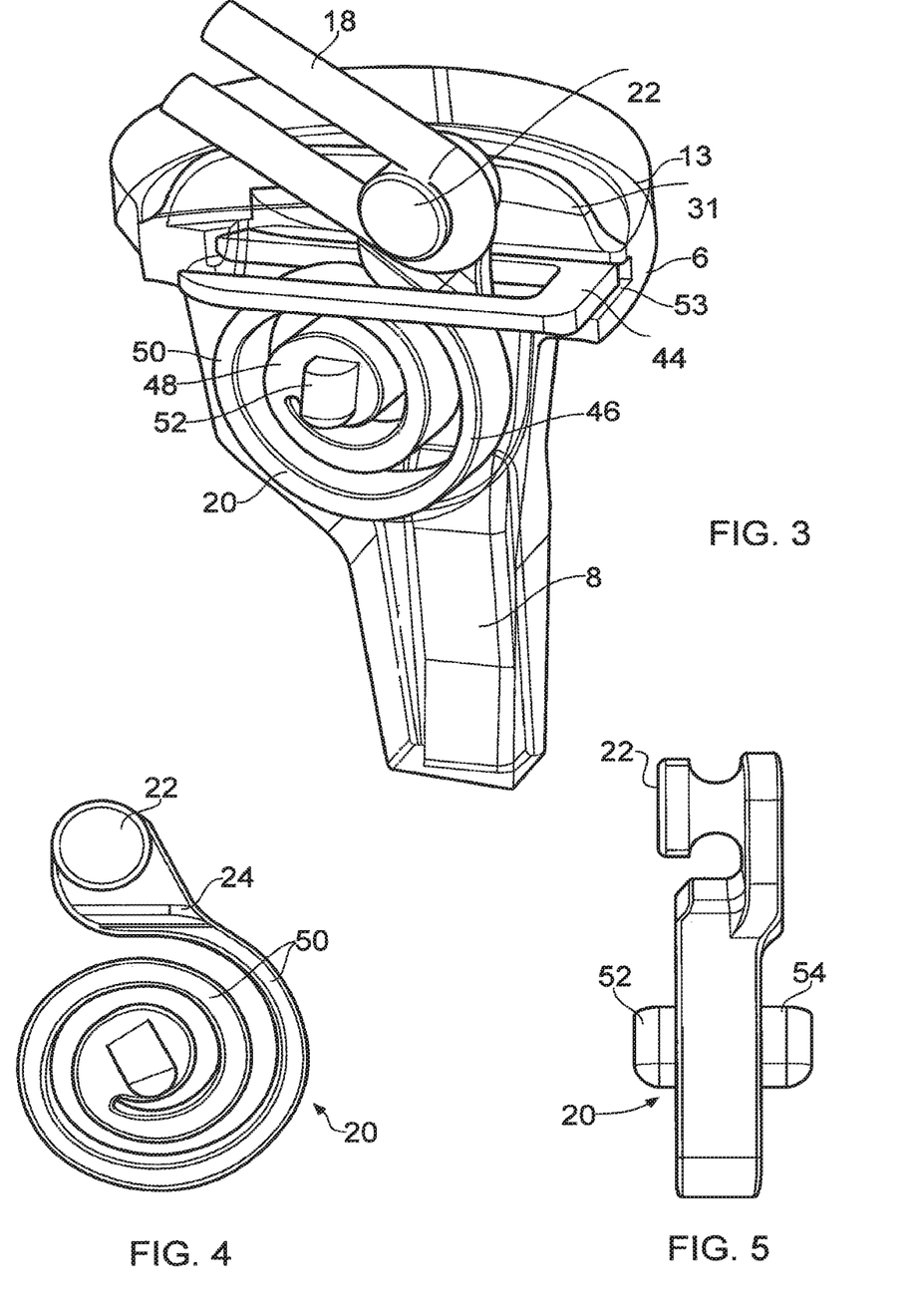
FIG. 3 is a partial sectional view of the ligament assembly of FIGS. 1 and 2.
FIG. 4 is a side view of a spiral spring of the ligament assembly of FIGS. 1 and 2.
FIG. 5 shews the spiral spring viewed in an anterior/posterior direction.

The spiral spring 20 is received within a bore 26 formed in the stem 8. The bore 26 extends through the tibial tray 4 into the stem 8 and is accessed through a mouth 30, flanked by walls 29, 31. The walls 29, 31 extend substantially in an anterior/posterior direction and project from the tibial component 4 substantially at right angles to the tibial bearing surface 14. The adjacent surfaces 33, 35 of the respective walls 29, 31, are smooth, and taper outwardly to accommodate the spiral spring 20 with some play. The walls 29, 31 ensure that the spiral spring 20 and artificial ligament 18 substantially do not interfere with the bearing components 12, 13 during normal articulation of the prosthesis. The edges of the walls 29, 31 may be radiused or chamfered to minimise damage in the event of impingement or dislocation of a component of the ligament assembly 2.

A slot 36, 38 is formed in each of the adjacent surfaces 33, 35 at the base of the walls 29, 31. The slots 36, 38 extend in parallel in an anterior/posterior direction on opposite sides of the mouth 30, and are open on their anterior ends so that they can receive a substantially U-shaped clip 44.

The spiral spring 20 comprises a single flat strip 46 which winds around a solid core 48 at its radially inner end to form a series of coils 50. The spiral spring 20 may be made from stainless steel or titanium or any other suitable material which may be machined, cast or wound and/or tempered to produce a spiral spring.

The solid core 48 of the spiral spring 20 is provided with a pair of elongate projections 52, 54 which extend outwardly in a medial-lateral direction from a plane defined by the coils 50 of the spiral spring 20.

Openings are formed in opposite sides of the bore 26 and extend substantially parallel to a longitudinal axis of the stem 8 into the side walls 29, 31 to form continuous grooves 56, 58. The grooves 56, 58 are shaped to closely receive the projections 52, 54 formed on the spiral spring 20.

In use of the ligament assembly 2, the tibia and femur are resected and the tibial component 4 and femoral component 10 are implanted. The spiral spring 20 is then inserted into the bore 26, such that the projections 52, 54 engage in the respective grooves 56, 58, and such that the bollard 22 projects beyond the walls 29, 31. The U-shaped dip 44 is then pushed into the slots 36, 38 to prevent the projections 52, 54 being withdrawn fully from the bore 26.

A loop formed in an end of the artificial ligament 18 is fixed onto the bollard 22 and the other end of the ligament is fixed to a bollard (not shown) or other suitable structure formed on the femoral component. In alternative embodiments, the other end of the ligament 18 may be fixed to bone by means of a conventional bone anchor and the spiral spring itself may be fitted to a more conventional bone anchor rather than to a component of a joint replacement prosthesis.

In joint replacement procedures it is important to balance the ligaments in the joint, so a kit may be provided which includes at feast two spiral springs 20, the spiral springs 20 having a different dimension, and/or different stiffness from one another. For example, the coils 50 of one of the springs 20 may be thicker or wider than those of the other spring, or the position of the bollard 22 relative to the projections 52, 54 on the core 48 may be different, so that the tension in the assembled ligament 18 is different, dependent on which spring 20 is used. The kit may also comprise one or more artificial ligaments and/or one or more bone anchors. At least one of the bone anchors may comprise a component of a joint replacement prosthesis. For example, it may comprise a tibial component 4.

As the projections 52, 54 are elongate and have rounded edges, they help to align the spiral spring 20 with the bore 26 during assembly. In addition, the projections 52, 54 prevent the core 48 of the spiral spring 20 from rotating relative to the tibial component 4. As the spiral spring is stiff in a medial/lateral direction, it is self supporting and is able to support the ligament 18 at the optimum position above the tibial tray 6. Also, as the core 48 cannot rotate, the coils 50 of the spring flex under loading from the ligament 18 to provide a degree of tensioning and/or shock absorbance. Consequently, the natural kinematics of the knee can be re-established, and sudden shock loads or extremes of articulation can be accommodated without overstressing the ligament.

The final step in implanting the prosthesis is to insert the appropriate size of bearing components 12, 13 between the femoral component 10 and the tibial component 4.

Any means of connection of the ligament 18 to the femoral component 10 is contemplated. For example, a boss or peg may be formed on the femoral component for attachment of the ligament 18. The end of the ligament 18 may be folded over and glued, sewn or otherwise fixed to form a loop (not shown). Alternatively, a hole or eye may be formed in the end of the ligament 18. The artificial ligament 20 may then be secured to the boss by passing the loop or eye over the boss. The boss may have an enlarged head and narrower stem to encourage stable fixation of the ligament once attached to the boss, such that it composes the bollard 22 described above.

The other end of the artificial ligament 18 is attached to the spiral spring 20 via the bollard 22. Any alternative means of connection between the other end of the ligament 18 and the spiral spring 20 is contemplated. For example, the end of the ligament 18 may pass wholly or substantially through an opening formed in the spiral spring 20 and may be prevented from passing back through the opening by a stop, which may take the form of an enlarged body, for example a spherical body, a cylinder, or any other appropriate form. Alternatively, the stop may comprise a knot formed in the end of the ligament 18, or the end of the ligament 18 may be moulded or glued into the radially outer end 24 of the spiral spring 20 or to an adapter attached to the end of the spiral spring 20.

The spiral spring 20 assists in replicating the natural stiffness of the ligament that is to be replaced. The characteristics of the spring, such as its extension under load are therefore selected to replicate those of the natural ACL.

It will be appreciated that with minor adaptation, the ligament assembly 2 could be used to repair a natural ligament or a ligament grown in-vitro, or could be adapted to another joint of the human or animal body.

To avoid unnecessary duplication of effort and repetition of text in the specification, certain features are described in relation to only one or several aspects or embodiments of the invention. However, it is to be understood that, where it is technically possible, features described in relation to any aspect or embodiment of the invention may also be used with any other aspect or embodiment of the invention.

The invention claimed is:

1. A method of implanting a ligament assembly comprising a resilient element, the method comprising:
    securing a bone anchor to a bone, the bone anchor including a resilient element at least partially disposed within a bore formed in the bone anchor; and
    connecting an end of a ligament to the resilient element such that the resilient element is operable to resist loads transmitted between the bone anchor and the ligament.

2. The method of claim 1, wherein the resilient element is operable to act as a cantilever and resist loads by virtue of the resistance to bending of the resilient element.

3. The method of claim 1, wherein the resilient element is operable to control an effective stiffness of the ligament.

4. The method of claim 1, further comprising securing a second bone anchor to a second bone.

5. The method of claim 4, further comprising connecting a second end of the ligament to the second bone anchor such that the ligament extends from the first bone anchor to the second bone anchor.

6. The method of claim 5, wherein the first bone anchor comprises a tibial prosthetic component.

7. The method of claim 6, wherein the second bone anchor comprises a femoral prosthetic component.

8. The method of claim 1, wherein the resilient element is formed from a metal.

9. The method of claim 8, wherein the resilient element comprises a spring.

10. The method of claim 1, wherein connecting the end of the ligament to the resilient element comprises securing a loop at the end of the ligament to a bollard extending from the resilient element.

11. A method of implanting a ligament assembly comprising a resilient element, the method comprising:
    implanting a bone anchor into a bone, wherein the bone anchor comprises a tibial prosthetic component;
    fixing a resilient element in a bore formed in the bone anchor; and
    connecting an end of a ligament to the resilient element such that the resilient element acts as a cantilever and resists loads transmitted between the bone anchor and the ligament by virtue of the resistance to bending of the resilient element.

12. The method of claim 11, further comprising, prior to fixing the resilient element in the bore formed in the bone anchor, selecting the resilient element from a set of interchangeable resilient elements.

13. The method of claim 12, wherein each resilient element in the set of interchangeable resilient elements comprises a different stiffness.

14. The method of claim 11, further comprising implanting a second bone anchor into a second bone.

15. The method of claim 14, wherein the second bone anchor comprises a femoral prosthetic component.

16. The method of claim 14, further comprising connecting a second end of the ligament to the second bone anchor.

17. A method of implanting a ligament assembly comprising a resilient element, the method comprising:

securing a prosthetic knee component to a femur or a tibia;

fixing a resilient element to the prosthetic knee component; and connecting an end of a ligament to the resilient element such that the resilient element acts as a cantilever and resists loads transmitted between the prosthetic knee component and the ligament by virtue of the resistance to bending of the resilient element.

18. The method of claim 17, further comprising, prior to fixing the resilient element to the prosthetic knee component, selecting the resilient element from a set of interchangeable resilient elements.

19. The method of claim 18, wherein each resilient element in the set of interchangeable resilient elements comprises a different stiffness.

\* \* \* \* \*

UNITED STATES PATENT AND TRADEMARK OFFICE
CERTIFICATE OF CORRECTION

| | | |
|---|---|---|
| PATENT NO. | : 11,253,350 B2 | Page 1 of 1 |
| APPLICATION NO. | : 16/676008 | |
| DATED | : February 22, 2022 | |
| INVENTOR(S) | : Dodd et al. | |

It is certified that error appears in the above-identified patent and that said Letters Patent is hereby corrected as shown below:

On the Title Page

In item (57), in "Abstract", in Column 2, Line 3, delete "m" and insert --as-- therefor In item (57), in "Abstract", in Column 2, Line 4, delete "toads" and insert --loads-- therefor On page 3, in Column 1, under "Other Publications", Line 9, after "16 pages.", insert --"U.S. Appl. No. 14/911,493 dated Feb. 11, 2016, Pat. No. 9,980,808, Ligament Assembly"
"U.S. Appl. No. 15/962,718 dated Apr. 25, 2018, Ligament Assembly"--

Signed and Sealed this
Second Day of August, 2022

Katherine Kelly Vidal
*Director of the United States Patent and Trademark Office*